United States Patent [19]

Hogue, Jr.

[11] 4,106,002
[45] Aug. 8, 1978

[54] TOURNIQUET PRESSURE MONITOR

[76] Inventor: Robert J. Hogue, Jr., 1809 NW. 47th St., Gainesville, Fla. 32605

[21] Appl. No.: 747,938

[22] Filed: Dec. 6, 1976

[51] Int. Cl.² .................. G08B 19/00; A61B 17/12
[52] U.S. Cl. .................. 340/626; 128/2.05 G; 128/327; 340/573
[58] Field of Search .................. 340/240, 236; 128/214 F, DIG. 12, 225, 226, 227, 228, 229, 235, 273, 276, 277, 278, 299, 327, 344, 2.05 G, 2.05 C

[56] References Cited

U.S. PATENT DOCUMENTS

| 3,410,268 | 11/1968 | Leucci .................. 128/227 |
| 3,648,694 | 3/1972 | Mogos et al. .................. 128/214 F |
| 3,877,838 | 4/1975 | Choy .................. 128/344 X |
| 3,982,540 | 9/1976 | Ross .................. 128/278 |

*Primary Examiner*—John W. Caldwell, Sr.
*Assistant Examiner*—Daniel Myer
*Attorney, Agent, or Firm*—Dunlap, Codding & McCarthy

[57] ABSTRACT

A monitor adapted for use with a pneumatic tourniquet having a pressure supply line, the monitor including an alarm which is actuated via a low pressure sensor or a high pressure sensor when the tourniquet pressure falls below or rises above predetermined minimum or maximum pressure levels, respectively, and an elapsed time indicator providing a perceivable indication of the total time during which the tourniquet has been pressurized.

2 Claims, 2 Drawing Figures

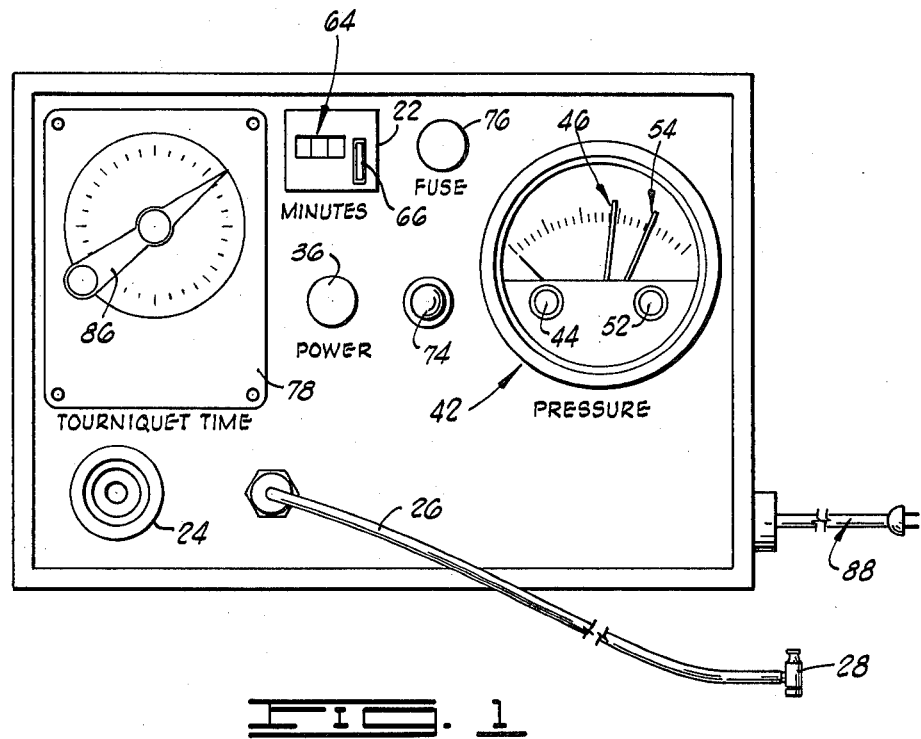
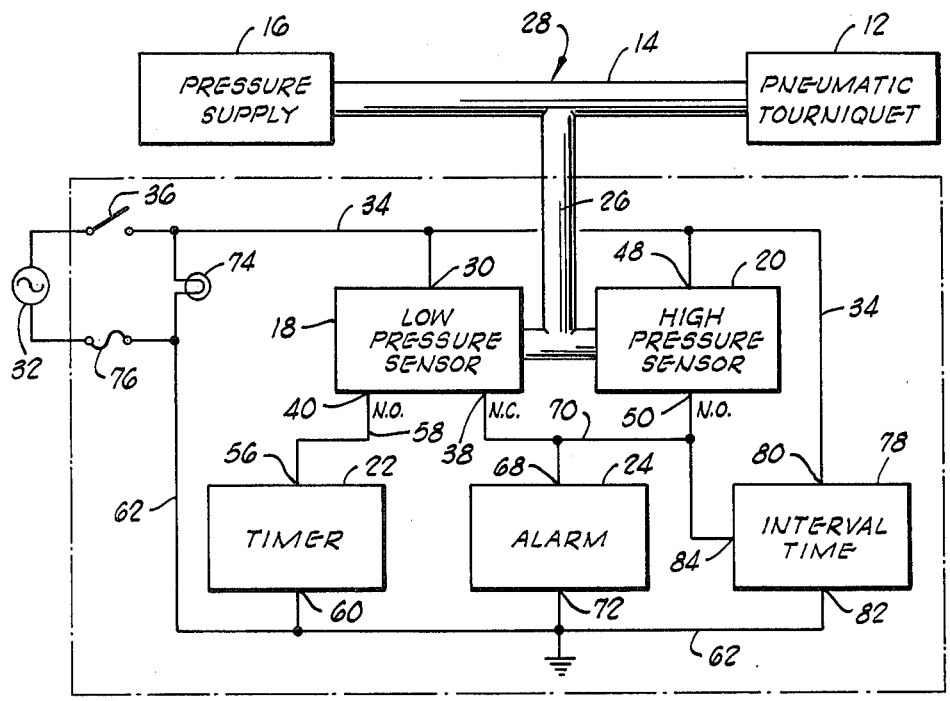

TOURNIQUET PRESSURE MONITOR

BACKGROUND OF THE INVENTION

1. Field of the Invention

This invention relates generally to improvements in tourniquet pressure monitors and, more particularly, but not by way of limitation, to a tourniquet pressure monitor having means to provide an alarm when the tourniquet pressure falls below or rises above predetermined minimum and maximum pressure levels, respectively, and a visually perceivable indication of the total time during which the tourniquet has been pressurized.

2. Description of the Prior Art

The use of the tourniquet to facilitate extremity surgery with a bloodless field has been common practice for years. Although the Esmarch bandage represented a significant improvement over the original screw-compression tourniquet devised by Petit in 1718, it was virtually impossible to control the degree of pressure exerted by the Esmarch bandage. This limitation when coupled with the destructive shearing force resulting from the rotational application of such a bandage, makes even the improved form of the Esmarch bandage devised by Von Langenbeck a truly dangerous means of obtaining a bloodless field for surgery in an extremity.

Following the introduction of the pneumatic tourniquet by Harvey Cushing, it was still common to have severe complications such as nerve palsy result from tourniquet use. Several studies have been published showing this damage to be a result of a localized block to conduction in the area where the tourniquet has been applied, with normal conduction occuring both proximally and distally in both sensory and motor fibers, thus establishing that the damage is a result of local compression of the nerve rather than ischemia. As a result of the determination that such damage is frequently the result of excessive pressure in the tourniquet system due to a faulty gage, it has been recommended that the pneumatic tourniquet gage be calibrated each day. Unfortunately, such daily calibration is often unperformed due to the heavy work load imposed upon operating room personnel.

In addition to the necessity of keeping the tourniquet pressure below a maximum pressure level, it is also important to prevent the tourniquet pressure from dropping to a level between systolic pressure and venous pressure thereby causing congestion which may be more harmful to the tissues distally then ischemia. Although the anesthetist is traditionally tasked with monitoring the tourniquet pressure, it is to be recognized that this function frequently suffers in view of the anesthetist's primary duty of administering the anesthetic.

In addition to nerve palsy, prolonged use of the pneumatic tourniquet may result in damage due to excessive ischemia time. Although it is generally agreed that ischemia time should be limited to two hours, times up to four hours have been reported without clinical evidence of permanent damage. In any event, the surgeon is responsible for deciding the maximum ischemia time at the beginning of each use of the tourniquet. However, the responsibility for monitoring ischemia time is usually delegated to one of the other operating room personnel, and has frequently been inadequately or inaccurately performed.

SUMMARY OF THE INVENTION

The present invention contemplates a tourniquet pressure monitor having means to provide an alarm when tourniquet pressure falls below or rises above predetermined minimum and maximum pressure levels, respectively, with a visually perceivable indication being provided of the total time during which the tourniquet has been pressurized.

It is an object of the present invention to provide a tourniquet pressure monitor which provides an alarm when the tourniquet pressure rises above a predetermined maximum pressure level.

Another object of the present invention is to provide a tourniquet pressure monitor which provides an alarm when the tourniquet pressure falls below a predetermined minimum pressure level.

A further object of the present invention is to provide a tourniquet pressure monitor which provides a visually perceivable indication of the total time during which a tourniquet has been pressurized.

Other objects and advantages of the invention will be evident from the following detailed description when read in conjunction with the accompanying drawings which illustrate the preferred embodiment of the invention.

BRIEF DESCRIPTION OF THE DRAWINGS

FIG. 1 is a plan view of a tourniquet pressure monitor constructed in accordance with the preferred embodiment of the present invention.

FIG. 2 is a diagrammatic illustration of the pneumatic tourniquet monitor showing the electrical schematic and the conduit connections.

DESCRIPTION OF THE PREFERRED EMBODIMENT

Referring to FIGS. 1 and 2, shown therein and referred to by the general reference number 10 is a monitor adapted for use with a pneumatic tourniquet 12 having a pressure supply line 14 connecting the tourniquet 12 to a pressure supply 16. The monitor 10 is comprised primarily of a low pressure sensor 18, a high pressure sensor 20, an elapsed time indicator 22 and an alarm 24.

The low pressure sensor 18 is connected to the pressure supply line 14 via a coupling conduit 26 and a conventional T-connector 28. The low pressure sensor 18 has an input terminal 30 connected to an AC power supply 32 via a conductor 34 and an on/off switch 36. The low pressure sensor 18 also has a normally-closed output terminal 38 and a normally-open output terminal 40. The low pressure sensor 18 is constructed in a conventional manner to connect the input terminal 30 thereof to the normally-closed output terminal 38 when the pressure applied thereto via the coupling conduit 26 is below a predetermined minimum pressure, and to connect the input terminal 30 thereof to the normally-open output terminal 40 when the pressure is above the predetermined minimum pressure. In the preferred embodiment, the low pressure sensor 18 forms one half of a pressure sensor assembly 42 with the predetermined minimum pressure being selected via a minimum pressure knob 44 which cooperates with an indicator needle 46 to provide a visual indication of the predetermined minimum pressure.

The high pressure sensor 20 is also connected to the pressure supply line 14 via the coupling conduit 26 and the T-connector 28. The high pressure sensor 20 has an input terminal 48 connected to the AC power supply 32 via the conductor 34 and the on/off switch 36. The high pressure sensor 20 also has a normally-open output terminal 50 and a normally-closed output terminal (not shown) which is not utilized in the present invention. The high pressure sensor 20 is constructed in a conventional manner to connect the input terminal 48 thereof to the normally-closed output terminal (not shown) when the pressure applied thereto via the coupling conduit 26 is below a predetermined maximum pressure, and to connect the input terminal 48 thereof to the normally-open output terminal 50 when the pressure is above the predetermined maximum pressure. In the preferred embodiment, the high pressure sensor 20 forms the other half of the pressure sensor assembly 42 with the predetermined maximum pressure being selected via a maximum pressure knob 52 which cooperates with an indicator needle 54 to provide a visual indication of the predetermined maximum pressure.

The elapsed time indicator 22 (referred to in FIG. 2 as "Timer") has a power terminal 56 connected to the normally-open output terminal 40 of the low pressure sensor 18 via a conductor 58, and a ground terminal 60 connected to the circuit ground via a conductor 62. The elapsed time indicator 22 is constructed in a conventional manner to provide a perceivable elapsed time indication via an output display 64 (see FIG. 1) which is indicative of the total time during which the elapsed time indicator 22 has AC power connected across the terminals 56 and 60 thereof. Preferably, the elasped time indicator 22 is provided with a reset button 66 so that the output display 64 may be conveniently reset to a predetermined starting value.

The alarm 24 has a power terminal 68 connected to the normally-closed output terminal 38 of the low pressure sensor 18 and to the normally-open output terminal 50 of the high pressure sensor 20 via a conductor 70, and a ground terminal 72 connected to the circuit ground via the conductor 62. The alarm 24 is constructed in a conventional manner to provide a perceivable output indication in the nature of an audible noise or a visual display in response to having AC power connected across the terminals 68 and 72 thereof.

In the preferred embodiment, a power indicator lamp 74 is interposed between the conductors 34 and 62 to provide a visual output indication of the connection of the monitor 10 to the AC power supply 32 via the on/off switch 36. In addition, the monitor 10 has a fuse 76 interposed in the conductor 62 generally between the lamp 74 and the AC power supply 32.

If desired, the monitor 10 may include an interval timer 78 (referred to in FIG. 2 as "Interval Time") having a power terminal 80 connected to the AC power supply 32 via the conductor 34, a ground terminal 82 connected to the circuit ground via the conductor 62, and an output terminal 84 connected to the power terminal 68 of the alarm 24 via the conductor 70. The interval timer 78 is constructed in a conventional manner to connect the power terminal 80 thereof to the output terminal 84 at predetermined time intervals selected via an interval timer knob 86.

A pressure sensor assembly 42 suitable for use in the present invention may be easily obtained commercially from Dwyer Instrument, Inc., of Michigan City, Indiana, under the name "Photohelic Pressure Gauge", No. 3210MP (120 VAC), circuit HH (117 VAC). Apparatus suitable for use as the elapsed time indicator 22 may be obtained commercially from the Herbach and Raderman Company of Philadelphia, Pennsylvania, under the name "Interval Timer-Fixed Interval (one minute)"; with the output display 64 being available from ITT General Controls, Inc., of Glendale, California, under the model No. C59BP302 (120 VAC). An interval timer 78 of suitable construction may be obtained from the Industrial Timer Corporation of Parsippany, New Jersey, under the Model No. TDAF3H (115 VAC). A satisfactory audio alarm 24 may be obtained from P.R. Mallory and Company under the Model No. SC110-7215.

OPERATION OF THE PREFERRED EMBODIMENT

Initially, the monitor 10 should be connected to the AC power supply 32 via a power cord 88 containing portions of the conductors 34 and 62. In addition, the T-connector 28 should be interposed in a conventional manner in the pressure supply line 14 generally between the pneumatic tourniquet 12 and the pressure supply 16. It will be assumed hereinafter that the pneumatic tourniquet 12 has been pressurized via the pressure supply 16 and that AC power has been connected to the conductor 34 via the on/off switch 36, as confirmed via the lamp 74. It will also be assumed hereinafter that appropriate operating room personnel have selected the predetermined minimum and maximum pressures via the minimum and maximum pressure knobs 44 and 52, respectively, and have reset the output display 64 of the elapsed time indicator 22 via the reset button 66.

If the pressure in the pressure supply line 14 is below the predetermined minimum pressure, the low pressure sensor 18 will operate to provide a low pressure signal by connecting the input terminal 30 thereof to the normally closed output terminal 38 thereof, thereby connecting AC power to the alarm 24 via the conductor 70. The alarm 24 will receive the low pressure signal in the form of AC power and provide a perceivable output indication in response to receiving the low pressure signal.

On the other hand, if the pressure in the pressure supply line 14 is at least equal to the predetermined minimum pressure, the low pressure sensor 18 will operate to provide a minimum pressure signal by connecting the input terminal 30 thereof to the normally-open output terminal 40 thereof, thereby connecting AC power to the elapsed time indicator 22 via the conductor 58. The elapsed time indicator 22 will receive the minimum pressure signal in the form of AC power and provide a perceivable elapsed time indication indicative of the total time during which the minimum pressure signal has been received.

If the pressure in the pressure supply line 14 is above the predetermined maximum pressure, the high pressure sensor 20 will effectively provide a high pressure signal by connecting the input terminal 48 thereof to the normally-open output terminal 50 thereof, thus connecting AC power to the alarm 24 via the conductor 70. The alarm 24 will receive the high pressure signal in the form of AC power and provide a perceivable output indication in response to receiving the high pressure signal.

If the interval timer 78 has been provided as a portion of the monitor 10, appropriate operating room personnel may initially select a convenient predetermined time interval via the interval timer knob 86. Thereafter, the interval timer 78 will periodically provide an elapsed time interval signal by connecting the power terminal 80 thereof to the output terminal 84 thereof at the end of each succeeding predetermined time interval, thereby periodically connecting AC power to the alarm 24 via the conductor 70. The alarm 24 will receive each elapsed time interval signal in the form of AC power and provide a perceivable output indication in response to receiving the respective elapsed time interval signal.

Changes may be made in the construction and the arrangement of the parts or the elements of the preferred embodiment as disclosed herein without departing from the spirit and scope of the invention as defined in the following claims.

What is claimed is:

1. A monitor adapted for use with a pneumatic tourniquet having a pressure supply line, the monitor comprising:
   low pressure sensing means connected to the pressure supply line, the low pressure sensing means sensing the pressure in the pressure supply line and providing a low pressure signal when the sensed pressure is below a predetermined minimum pressure and a minimum pressure signal when the sensed pressure is at least equal to the predetermined minimum pressure;
   high pressure sensing means connected to the pressure supply line, the high pressure sensing means sensing the pressure in the pressure supply line and providing a high pressure signal when the sensed pressure is above a predetermined maximum pressure;
   elapsed time indicating means connected to the low pressure sensing means, the elapsed time indicating means receiving the minimum pressure signal and providing a perceivable elapsed time indication indicative of the total time during which the minimum pressure signal has been received; and
   alarm means connected to the low pressure sensing means and to the high pressure sensing means, the alarm means receiving the low pressure signal and the high pressure signal and providing a perceivable output indication in response to receiving at least one of the low pressure signal and the high pressure signal.

2. The monitor of claim 1 further defined to include:
   interval timing means connected to the alarm means, the interval timing means providing an elapsed time interval signal at the end of a predetermined time interval; and
   wherein the alarm means is further characterized as being connected to the interval timing means, the alarm means receiving the elapsed time interval signal and providing a perceivable output indicator in response to receiving the elapsed time interval signal.

* * * * *